(12) United States Patent
Thiel et al.

(10) Patent No.: US 10,057,560 B2
(45) Date of Patent: Aug. 21, 2018

(54) METHOD AND DEVICE FOR INTRAORAL THREE-DIMENSIONAL SURVEYING

(71) Applicant: DENTSPLY SIRONA Inc., York, PA (US)

(72) Inventors: Frank Thiel, Ober-Ramstadt (DE); Joachim Pfeiffer, Bensheim (DE)

(73) Assignee: DENTSPLY SIRONA INC., York, PA (US)

( * ) Notice: Subject to any disclaimer, the term of this patent is extended or adjusted under 35 U.S.C. 154(b) by 380 days.

(21) Appl. No.: 14/614,673

(22) Filed: Feb. 5, 2015

(65) Prior Publication Data

US 2015/0222878 A1 Aug. 6, 2015

(30) Foreign Application Priority Data

Feb. 5, 2014 (EP) ..................................... 14153942

(51) Int. Cl.
*H04N 13/02* (2006.01)
*H04N 13/00* (2018.01)
(Continued)

(52) U.S. Cl.
CPC ......... *H04N 13/026* (2013.01); *A61B 5/0064* (2013.01); *A61B 5/4547* (2013.01); *A61C 9/006* (2013.01); *A61C 9/0053* (2013.01); *A61C 19/04* (2013.01); *G01B 11/2518* (2013.01); *G06T 7/55* (2017.01); *H04N 13/0055* (2013.01); *H04N 13/0296* (2013.01); *A61B 5/0073* (2013.01);
(Continued)

(58) Field of Classification Search
None
See application file for complete search history.

(56) References Cited

U.S. PATENT DOCUMENTS 4,837,732 A 6/1989 Brandestini et al.
2006/0246393 A1 11/2006 Eiff et al.
(Continued)

FOREIGN PATENT DOCUMENTS

DE  10 2012 100 953 A1  8/2013
EP  1 277 432 A1  1/2003
EP  1 716 816 A1  11/2006

OTHER PUBLICATIONS

European Search Report dated Jun. 5, 2014, in European Patent Application No. 14153942.9.
(Continued)

*Primary Examiner* — Kate Luo
(74) *Attorney, Agent, or Firm* — David A. Zdurne; Douglas J. Hura; Leana Levin

(57) ABSTRACT

The method for optical three-dimensional surveying using an intraoral camera (2), wherein the intraoral camera (2) provides that a 3D image is created from at least one of the 2D recorded images or from at least one of the sequences, and wherein a plurality of all the 2D recorded images and/or sequences created in a first operating mode (M1) are used to create at least one overall 3D image. In addition, the method provides that a selection is made between the first operating mode (M1) and a second operating mode (M2), wherein a plurality of all 2D recorded images and/or sequences created during an interval of time (T) are used in the second operating mode (M2) to create at least one 3D image immediately before and/or after a triggering command (A).

26 Claims, 2 Drawing Sheets

(51) Int. Cl.
*A61C 19/04* (2006.01)
*A61C 9/00* (2006.01)
*A61B 5/00* (2006.01)
*G01B 11/25* (2006.01)
*G06T 7/55* (2017.01)

(52) U.S. Cl.
CPC ...... *A61B 2576/00* (2013.01); *G01B 2210/52* (2013.01); *G06T 2207/30036* (2013.01)

(56) References Cited

U.S. PATENT DOCUMENTS

| | | | |
|---|---|---|---|
| 2009/0021745 A1* | 1/2009 | Tamura | A61B 5/0059 356/479 |
| 2010/0158490 A1 | 6/2010 | Pfeiffer et al. | |
| 2010/0209002 A1* | 8/2010 | Thiel | A61B 5/0064 382/206 |
| 2015/0002649 A1 | 1/2015 | Nowak et al. | |

OTHER PUBLICATIONS

Christin Bunnileipzig, "The Ease of the Scannens", CAD/CAM in Praxis Und Labor, 2012, pp. 045-047.
Dr. Jan Bjerg Andersen, "Digital Castings of the Next Generation", 3Shape TRIOS, 2012.
Joachim Pfeiffer, Axel Schwotzer, "Dreidimensionale Optische Vermessung von Zahnen", 1996, pp. 254-260, tm-Technisches Messen 63.

* cited by examiner

US 10,057,560 B2

METHOD AND DEVICE FOR INTRAORAL THREE-DIMENSIONAL SURVEYING

CROSS-REFERENCE TO RELATED APPLICATIONS

This application claims priority to EP 14 153 942.9 filed Feb. 5, 2014.

BACKGROUND OF THE INVENTION

Field of the Invention

The invention relates to a device for intraoral three-dimensional optical surveying and a method for optical three-dimensional surveying using an intraoral camera, wherein the camera creates 2D recorded images in rapid chronological order and wherein a 3D image is created from at least one 2D recorded image taken by the surveying camera. In a first operating mode, an overall 3D image is created from a plurality of all the 2D recorded images and/or sequences created.

Description of the Related Art

Various types of intraoral 3D measuring cameras are known. A first type of intraoral 3D surveying camera creates a 3D image based on a plurality of images of the object from the same perspective, as is known from tm—Technisches Messen 63 (1996) 6, p. 254-260. This type of camera must be held as still as possible for a certain period of time, which is needed for detecting the multiple images.

This makes great demands on a user. There is a risk of creating shaky images, which are therefore useless, and/or having to repeat the surveying multiple times.

A second type of intraoral 3D measuring camera, as described in the applicant's company brochure by Christian Bunn, "Die Leichtigkeit des Scannens" [Ease of Scanning] in CAD/CAM in practice and in the laboratory, 2012, creates a 3D image on the basis of a single recording. Accordingly, then it is not necessary to hold the camera still, at least if the single image is recorded rapidly enough, for example, in less than one second. This makes it possible to record images in motion and thus to continuously survey regions that are larger than the visual field of the camera. The camera is therefore moved slowly over the region to be surveyed and individual recorded images are created continuously. Then a 3D image can be created from each individual recorded image, and the 3D images thereby created can be combined into one three-dimensional image of the entire region.

A third type of intraoral 3D measuring camera, as known from the applicant's company brochure, 3 Shape A/S, Jan Bjorg Andersen, "Digitate Abdrücke der nächsten Generation" [Digital Impressions of the Next Generation], 2012, creates a 3D image from a sequence of multiple recorded images, such as the first type described, but the recording frequency is so rapid that it takes much less than one second to record a sequence, for example. In addition, effects that occur due to movement of the camera can be computationally neutralized, for example, in the creation of one 3D recorded image from a plurality of recorded images of a sequence, can be neutralized. It is possible in this way to also use 3D measuring cameras of the third type like many cameras of the second type for continuous recording while moving the camera and/or for continuous surveying of larger regions.

The continuous recording mode for surveying larger regions by continuous movement of the camera over the region to be surveyed, which intraoral 3D measuring cameras of the second and third types provide, also makes great demands on the user. For example, one should avoid including movable regions such as the tongue, the cheeks or the lips in the recording because, if they move between the different recordings and/or recording sequences, they make it difficult to join the individual 3D recorded images and may even falsify or prevent such joining. Control of the data volume generated is also more difficult for the user, such that a high data volume, i.e., an unnecessarily large number of recorded images created, can lead to delays in creation of the 3D recorded images and/or the overall 3D recorded images.

The object of the present invention is therefore to make available an intraoral 3D camera and a corresponding method, which make it possible to record larger regions in particular in the simplest and most reliable possible manner.

BRIEF SUMMARY OF THE INVENTION

This object is achieved by a method for optical three-dimensional surveying using an intraoral camera, wherein the intraoral camera creates individual 2D recorded images or sequences of a plurality of successively created 2D recorded images, and wherein a 3D image is created from at least one of the individual 2D recorded images or from at least one of the sequences. A choice is made between a first and a second operating mode. In the first operating mode, a plurality of all the individual 2D recorded images created and/or sequences created is used to create an overall 3D image. In the second operating mode, a plurality of all the 2D recorded images and/or sequences created during an interval of time is/are used to generate an overall 3D image, wherein the interval of time is immediately before and/or after a triggering command.

Depending on the type of recorded image, a 3D image can be created from at least one 2D image or from at least one sequence of 2D images. The surveying result referred to as an overall 3D image can be created and/or compiled from at least one such 3D image. However, it is also possible to create the overall 3D image directly from the 2D recorded images, i.e., from at least one 2D recorded image or at least one sequence of 2D recorded images.

The two operating modes make it possible for the user to select between a type of constant 3D video operation and a type of "point-and-click" operation.

In the first operating mode, i.e., 3D video operation, the recording runs continuously, for example, from the start of operation of the camera until it is turned off. The 2D recorded images or sequences are created continuously and a 3D image is created for each 2D recorded image and/or for each sequence. The 3D images created can then be compiled continuously, gradually, or after the end of the entire recording procedure to form an overall 3D image.

The second operating mode, the "point-and-click" operation, provides in that regard that, although 2D recorded images are created continuously, the 2D recorded images are also processed further only after a triggering command. For example, this allows the user to position the camera in stable fashion over the object to be recorded before starting the surveying of same, and 3D images are created from the 2D recorded images and/or sequences, which are then created continuously and compiled, gradually, or after conclusion of the entire surveying and/or sequence of the time interval to form an overall 3D image. With a quick choice accordingly, mere three-dimensional photography of a region of the object that has been targeted can also be achieved in this way by recording at least one 2D recorded image or at least one sequence of 2D recorded images during the interval of time for calculation of precisely one 3D image, and the 3D image calculated from this is then stored as an overall 3D image. The overall 3D image presented as the result of the surveying may thus be compiled from one or more 3D images. The second mode of operation thus makes it possible to better control both the recorded image section and the data volume.

To facilitate the positioning, for example, the 2D recorded images that are created or the additional 2D recorded images created with the camera between two individual 2D recorded images or between two sequences are displayed for the user on a screen, for example. Such preview functions are already known. Depending on the survey technique, these additional 2D recorded images may be created, for example, after opening a grating that is situated in an illumination beam for projection of patterns or with a grating that is moving very rapidly at a right angle to an illumination beam.

In advantageous fashion, the triggering command is generated by operation of a foot-activated switch.

A foot-activated switch makes it possible to issue the triggering command in a controlled manner without thereby interfering with the most controlled possible movement of the handheld camera.

The triggering command is advantageously generated by a motion sensor when the latter detects that the surveying camera is not moving.

This makes it possible to prevent wobbling and/or jerky movements of the camera, which are caused by operation of a switch by foot or with a free finger or a free hand.

The camera may be moved in a very easy-going manner and may be positioned over the desired scene without generating any data. If the user has found the desired scene and/or has positioned the camera in the desired position, he must simply hold the camera still briefly to trigger the surveying and then move the camera over a region to be surveyed in a controlled manner, for example.

While recording from at least two 2D successively created recorded images, a shakiness index is advantageously determined and compared with a limit value, and a triggering command is generated when the value thus determined is below the limit value.

Determining a number of jerks from the 2D recorded images created makes it possible to trigger the triggering command by holding the camera still without requiring an additional component such as a sensor.

The individual 2D recorded images or sequences are advantageously stored one after the other in a temporary memory device, where a number of individual 2D recorded images and/or sequences are stored and, after reaching that number, individual 2D recorded images and/or sequences already stored are overwritten by new individual 2D recorded images and/or sequences.

At least temporary storage of the 2D recorded images in a temporary memory device permits a relatively free choice of the ratio of the recording interval of time and the triggering command, for example. Requirements regarding the size of the temporary memory can be reduced by this overwriting. Such a temporary memory device may be placed directly in the handheld camera, for example. Memory or temporary memory here is understood to refer to any medium which is capable of recording image data of at least one image and from which image data of at least one image can be read out.

After the triggering command, all the 2D recorded images created within an interval of time preceding the triggering command or all the 2D recorded images created within an interval of time following the triggering command or all the 2D recorded images created within an interval of time comprising the point in time of the triggering command are advantageously transferred to a memory device.

For further processing and/or for documentation, the data for the 3D images and/or the overall 3D image are stored in a memory device. If the camera is operated in the second operating mode, then the data volume can be controlled by the fact that only the data in the recording interval of time are transferred to the memory device, for example, directly or from a temporary memory device. The recording interval of time is determined by the triggering command. It may be either an interval of time, which directly follows the point in time of creation of the triggering command, or it may also be an interval of time around the triggering command or even an interval of time directly preceding the time of creating the triggering command. The memory device may be placed, for example, in the camera itself or in a central processing unit or the like, wherein the data may be transmitted by means of a cable or by wireless transmission, for example.

The 2D recorded images or additionally created 2D recorded images are advantageously displayed one after the other on a display screen.

This can facilitate the orientation and/or positioning of the camera. This may also permit monitoring of the position of the camera during the surveying.

Advantageously the at least one 3D image and/or the overall 3D image is/are displayed on a display screen.

If the 3D images created from the 2D recorded images created are displayed directly one after the other, then the position of the camera during the surveying can be controlled using these. It is also possible to continuously combine the 3D images that are created, so that the user can monitor the result and/or the intermediate result of his surveying, namely the creation of the overall 3D image.

The interval of time advantageously has a predetermined or predeterminable duration.

The data volume is limited in this way. The interval of time may be set or selected in advance, for example. The end may be displayed for the user, for example, on a display screen or by a lamp or similar device on the camera or also by a tone.

The interval of time also advantageously ends after a stop command.

In this way, the user can adjust the recording duration to his needs, so that the data volume in particular can be minimized. The stop command may be generated, for example, by a switch on the camera, by a foot-operated switch or by means of a verbal command and a corresponding acoustic sensor. It is particularly simple to generate the stop command in the same way as the triggering command. For example, if the triggering command is generated by means of a foot-operated switch, then the subsequent actuation of the foot-operated switch may generate the stop command.

In addition, the invention relates to a device for intraoral three-dimensional optical surveying and has a handheld intraoral camera and at least one memory device placed inside or outside the camera. The 2D recorded images can be created continuously using this device. In addition, the device exhibits means for selecting a first operating mode or a second operating mode as well as a triggering unit.

Expansion of an intraoral camera for continuous measurements, also referred to as on-the-fly measurements, by including a triggering unit and selection means with regard to the operating mode, makes it easier for a user to monitor the data volume and the image section.

The triggering unit is advantageously a foot-operated switch, which is a particularly simple means for generating a triggering command.

The triggering unit advantageously comprises a motion sensor placed on the surveying camera and a comparison unit, wherein a motion value that is comparable to a preadjustable comparison value can be created by the motion sensor by means of a comparison unit.

It is simple in this way to detect that the camera is being held still.

The triggering unit advantageously has a shakiness analysis unit for determining a shakiness index from at least two recorded images created.

A shakiness analysis unit can determine if the camera is being held still on the basis of two recorded images created. Therefore, no additional sensors are needed.

The device advantageously includes a display screen on which recorded images created using the surveying camera can be displayed side by side and/or one after the other.

The positioning and/or guidance of the camera can be controlled easily in this way.

The device advantageously has a stop unit, which makes it possible for the user to monitor the duration of recording. It is particularly simple if the stop unit is identical to the triggering unit, i.e., if the triggering unit also functions as a stop unit.

BRIEF DESCRIPTION OF THE DRAWINGS

The device according to the invention and the method according to the invention will now be explained on the basis of the drawings, which show.

DETAILED DESCRIPTION OF THE INVENTION

Figure 1:
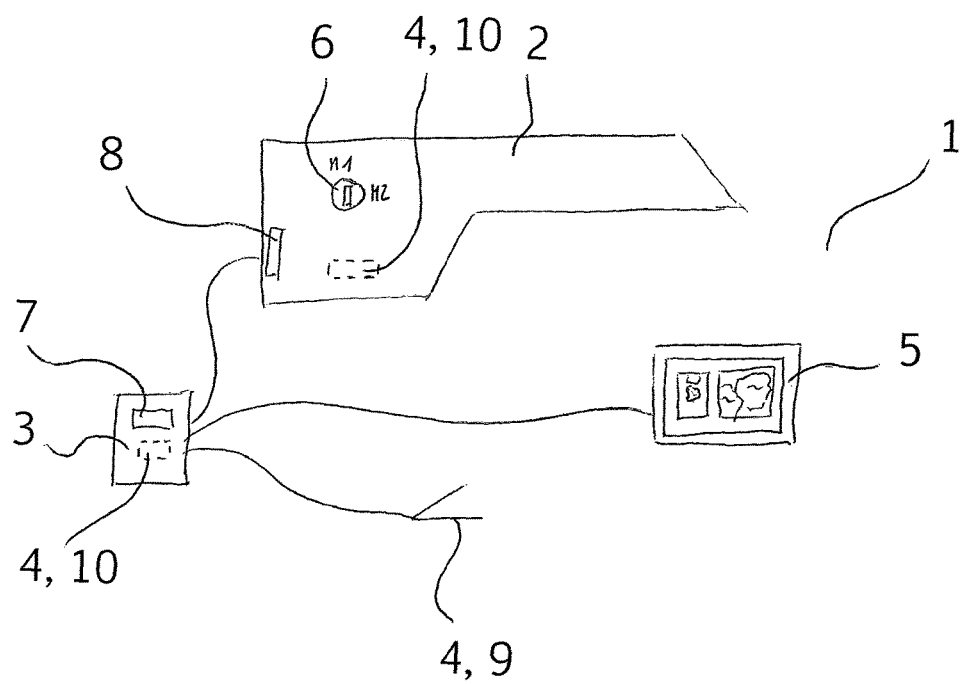
FIG. 1 a device for intraoral three-dimensional optical surveying.

A device 1 for intraoral three-dimensional optical surveying is diagrammed in FIG. 1, comprising a handheld intraoral camera 2, a central processing unit 3, which includes a triggering unit 4 designed as a foot-operated switch and a display means 5 designed as a display screen. The intraoral camera 2 has a switch as the means 6 for selecting an operating mode M1, M2.

The camera 2 may be, for example, a surveying unit based on triangulation, which measures an object to be recorded by means of patterns projected onto it. The recording process, i.e., projection of the pattern and detection of the backscattered light as a 2D recorded image, for example, is started as soon as the camera is taken from a holder or is switched on, for example. The camera 2 then detects 2D recorded images continuously.

Depending on the surveying method, a 3D image can be created from a single 2D recorded image or from a sequence of several successive 2D recorded images that have been created. All the 3D images that are created may be joined together either after conclusion of the recording process or even a little at a time during the recording process to form an overall 3D image.

Instead of being designed as a foot-operated switch, the triggering unit 4 may also be designed as a motion sensor placed on the intraoral camera 2 and also as a comparison unit, as diagrammed in FIG. 1 with the dotted line. The comparison unit may be placed either in the central processing unit 3 or also in the camera 2, as shown with the broken line in FIG. 1.

Figure 2:
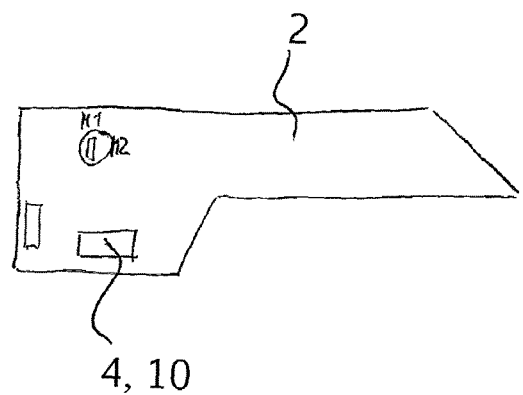
FIG. 2 a device having a triggering unit designed as a shakiness analysis unit.

In addition, it is possible to design the triggering unit 4 as a shakiness analysis unit 10, which may be placed in the intraoral camera 2, for example, as shown in FIG. 2. The shakiness analysis unit may, however, also be placed in the central processing unit 3 and/or may be a part of the central processing unit. A shakiness index V is determined from at least two 2D recorded images created successively by means of the shakiness analysis unit and compared with a limit value G. A triggering command A is then issued by the triggering unit 4, which is designed as a shakiness analysis unit 10, when the shakiness index V thus determined is lower than the limit value G, as shown in FIG. 5.

Figure 5:
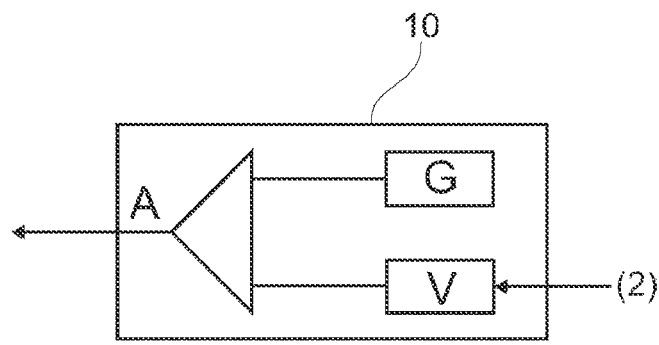
FIG. 5 a simplified block diagram of the shakiness analysis unit.

FIG. 5 shows a simplified block diagram of the shakiness analysis unit 10. It forms the shakiness index V from the signal, represented as an arrow, of the intraoral camera 2. In the comparison unit, which is represented as a triangle, the shakiness index V is compared with a stored limit value G to generate the triggering command A from the result of the comparison. The method according to the invention provides that a user can select between a first operating mode M1 and a second operating mode M2 by means of a means 6, designed as a switch, for example.

In the first operating mode M1, the continuously generated and/or detected 2D recorded images are transferred to a memory device 7 placed in the central processing unit 3, for example. The memory device 7 might also be placed in the camera 2 itself, if it is designed to be small enough and light enough. An overall 3D image is generated at least from a plurality of all the 2D recorded images transferred to the memory device 7, wherein a 3D image is calculated for this purpose from a single 2D recorded image or from a sequence, and the calculated 3D images are joined. Some of the transferred 2D recorded images may be discarded intentionally because of poor quality, for example, if the number of data points is low.

Figure 3:
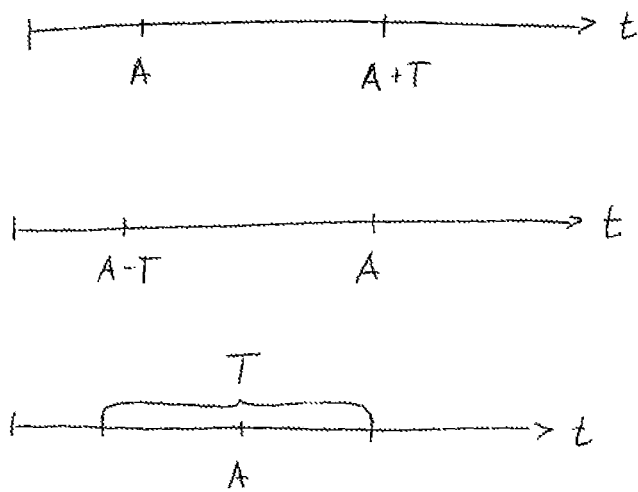
FIG. 3 an interval of time in relation to a triggering command.

In the second operating mode M2, 2D recorded images are not transferred to the memory device 7 until a triggering command A is issued, namely all the 2D recorded images detected during an interval of time T, which depends on the time of the triggering command A. At least a plurality of these 2D recorded images transferred to the memory device 7 is used for the overall 3D image. Some of the 3D images may be discarded because of poor quality, for example. The interval of time T may directly follow the time of the triggering command, for example, as diagrammed in FIG. 3 above. The interval of time T may also directly precede the time of the triggering command A, as represented at the center of FIG. 3. Alternatively, the interval of time T may also comprise the time of the triggering command A, as diagrammed at the bottom of FIG. 3.

In the case of the last two variants, it is necessary to set up a temporary memory device 8, for example, inside the camera 2 or in the central processing unit 3 or to also use the memory device 7 as a temporary memory device and to always store the most recent 2D recorded images in this temporary memory device 8. The temporary memory device 8 must be designed large enough so that all the desired 2D recorded images that have already been created are still present and can still be transferred to the memory device 7 at the time of the triggering command A, depending on the choice of the interval of time T relative to the time of the triggering command A.

Figure 4:
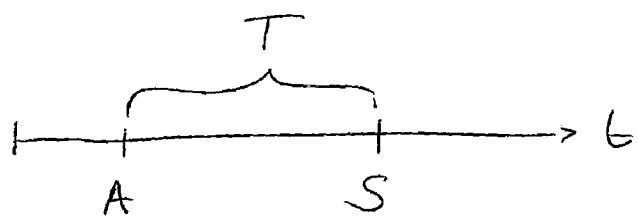
FIG. 4 an interval of time defined by a triggering command and a stop command.

The interval of time T, i.e., its duration, may be defined or selected in advance, for example. It is also possible to terminate the interval of time by a stop command S. As diagrammed in FIG. 4, the interval of time may begin with the triggering command A, for example, and may end with the stop command S.

The device 1 may therefore have a stop unit 9. This may be designed, for example, as a foot-operated switch and/or may be identical to the triggering unit 4 diagrammed in FIG. 1.

Regardless of the operating mode M1, M2, the 2D recorded images thus created or any 2D recorded images created in addition, may be displayed one after the other on a display device 5, so that a type of 2D video is made available to the user for orientation purposes. In addition, it is also possible to display all the 3D images already created on a display device 5, for example, simultaneously with the 2D recorded images. The 3D images may be displayed one after the other, thus forming a type of 3D video. It is also possible to combine the 3D images only gradually and to always display the overall 3D image that has already been compiled, so that the user can observe the formation of the overall 3D image even during the recording process.

LIST OF REFERENCE NUMERALS

1 device for intraoral three-dimensional optical surveying
2 intraoral camera
3 central processing unit
4 triggering unit
5 display device
6 means for selecting an operating mode
7 memory device
8 temporary memory device
9 stop unit
10 shakiness analysis unit
A triggering command
G limit value
M1 first operating mode
M2 second operating mode
S stop command
V shakiness index
T interval of time

The invention claimed is:

1. A method comprising:
providing a dental imaging apparatus that includes a central processing unit constructed to generate an overall three-dimensional image in a first mode and another overall three-dimensional image in a second mode,
generating the overall three-dimensional image in the first mode from a plurality of images recording by an intraoral camera during an imaging operation, wherein the plurality of images comprise intermediate three-dimensional images,
wherein said intermediate three-dimensional images are created from individual 2D recorded images or sequences of a plurality of successively created 2D recorded images,
wherein said 2D recorded images are created in chronological order;
generating the another overall three-dimensional image in the second mode from a subset of the plurality of images, the subset of the plurality of images being recorded during a specific time interval of the imaging operation,
wherein the specific time interval:
(i) precedes a time when a triggering command is issued,
(ii) follows the time when the triggering command is issued, or
(iii) comprises the time when the triggering command is issued and
controlling a high data volume in the second mode by transferring the subset of the plurality of images to a memory device only after the triggering command is issued such that a recorded image section can be monitored,
wherein in the first mode, said intermediate three-dimensional images are compiled continuously, gradually, or after the end of a first recording procedure to form said overall three-dimensional image and
wherein in the second mode, said intermediate three-dimensional images are compiled continuously, gradually, or after the end of a second recording procedure to form said another overall three-dimensional image.

2. The method according to claim 1, wherein the central processing unit is further constructed to receive the subset of the plurality of images after the triggering command is issued.

3. The method according to claim 2, wherein the central processing unit is further constructed to receive the subset of the plurality of images from a temporary memory constructed to store at least a portion of the plurality of images.

4. The method according to claim 1, wherein the central processing unit is further constructed to transmit the triggering command to the intraoral camera.

5. The method according to claim 4, wherein the central processing unit is further constructed to receive the triggering command from a foot-operated switch.

6. The method according to claim 1, further comprising:
providing the dental imaging apparatus with a shakiness analysis unit constructed to (i) determine a shakiness index based on at least two of the plurality of images, and (ii) issue the triggering command if the shakiness index is less than a predetermined value.

7. The method according to claim 1, further comprising:
providing the dental imaging apparatus with a display device constructed to display the subset of the plurality of images one after the other.

8. The method according to claim 1, further comprising:
providing the dental imaging apparatus with a display device constructed to display the overall three-dimensional image or the another overall three-dimensional image.

9. The method according to claim 1, wherein a length of the specific time interval is predetermined.

10. The method according to claim 1, wherein the central processing unit is further constructed to transmit a stop command to the intraoral camera, wherein the specific time interval begins with the triggering command and ends with the stop command.

11. A dental imaging apparatus, comprising:
a central processing unit constructed to generate an overall three-dimensional image in a first mode and another overall three-dimensional image in a second mode,
wherein, in the first mode, the central processing unit generates the overall three-dimensional image from a plurality of images recording by an intraoral camera during an imaging operation, wherein the plurality of images comprise intermediate three-dimensional images,
wherein said intermediate three-dimensional images are created from individual 2D recorded images or sequences of a plurality of successively created 2D recorded images
wherein said 2D recorded images are created in chronological order and
wherein, in the second mode, the central processing unit generates the another overall three-dimensional image from a subset of the plurality of images, the subset of the plurality of images being recorded during a specific time interval of the imaging operation,
wherein the specific time interval:
(i) precedes a time when a triggering command is issued,
(ii) follows the time when the triggering command is issued, or
(iii) comprises the time when the triggering command is issued
wherein the central processing unit is configured to control a high data volume in the second mode by transferring the subset of the plurality of images to a memory device only after the triggering command is issued such that a recorded image section can be monitored,
wherein in the first mode said intermediate three-dimensional images are compiled continuously, gradually, or after the end of a first recording procedure to form said overall three-dimensional image and
wherein in the second mode, said intermediate three-dimensional images are compiled continuously, gradually, or after the end of a second recording procedure to form said another overall three-dimensional image.

12. The dental imaging apparatus according to claim 11, wherein the central processing unit is further constructed to receive the subset of the plurality of images after the triggering command is issued.

13. The dental imaging apparatus according to claim 11, wherein the central processing unit is further constructed to transmit the triggering command to the intraoral camera.

14. The dental imaging apparatus according to claim 13, wherein the central processing unit is further constructed to receive the triggering command from a foot-operated switch.

15. The dental imaging apparatus according to claim 11, further comprising:
a shakiness analysis unit,
wherein the shakiness analysis unit is constructed to determine a shakiness index based on at least two of the plurality of images, and issue the triggering command if the shakiness index is less than a predetermined value.

16. The dental imaging apparatus according to claim 11, wherein the central processing unit is further constructed to receive the subset of the plurality of images from a temporary memory constructed to store at least a portion of the plurality of images.

17. The dental imaging apparatus according to claim 11, further comprising:
a display device constructed to display the subset of the plurality of images one after the other.

18. The dental imaging apparatus according to claim 11, further comprising:
a display device constructed to display the overall three-dimensional image or the another overall three-dimensional image.

19. The dental imaging apparatus according to claim 11, wherein a length of the specific time interval is predetermined.

20. The dental imaging apparatus according to claim 11, wherein the central processing unit is further constructed to transmit a stop command to the intraoral camera, wherein the specific time interval begins with the triggering command and ends with the stop command.

21. A dental imaging system, comprising:
an intraoral camera constructed to generate a plurality of images and configured to operate in a first mode and a second mode; and
a central processing unit constructed to receive one or more of the plurality of images and generate an overall three-dimensional image, in the first mode, and another overall three-dimensional image, in the second mode,
wherein, in the first mode, the central processing unit generates the overall three-dimensional image from the plurality of images, wherein the plurality of images comprise intermediate three-dimensional images,
wherein said intermediate three-dimensional images are created from individual 2D recorded images or sequences of a plurality of successively created 2D recorded images
wherein said 2D recorded images are created in chronological order and
wherein, in the second mode, the central processing unit generates the another overall three-dimensional image from a subset of the plurality of images recorded during a specific time interval,
wherein the specific time interval:
(i) precedes a time when triggering command is issued,
(ii) follows the time when the triggering command is issued, or
(iii) comprises the time when the triggering command is issued
wherein the central processing unit is configured to control a high data volume in the second mode by transferring the subset of the plurality of images to a memory device only after the triggering command is issued such that a recorded image section can be monitored,
wherein in the first mode said intermediate three-dimensional images are compiled continuously, gradually, or after the end of a first recording procedure to form said overall three-dimensional image and
wherein in the second mode, said intermediate three-dimensional images are compiled continuously, gradually, or after the end of a second recording procedure to form said another overall three-dimensional image.

22. The dental imaging system according to claim 21, wherein the intraoral camera includes a switch for selecting between the first mode and the second mode.

23. The dental imaging system according to claim 21, further comprising:
a foot-operated switch constructed to generate the triggering command, wherein the central processing unit is further constructed to receive the triggering command and transmit the triggering command to the intraoral camera.

24. The dental imaging system according to claim 21, further comprising:
- a motion sensor constructed to detect motion of the intraoral camera,
- wherein the triggering command is issued when the motion sensor detects that the intraoral camera is still.

25. The dental imaging system according to claim 21, further comprising:
- a shakiness analysis unit constructed to determine a shakiness index based on at least two of the plurality of images, wherein the triggering command is issued by the shakiness analysis unit when the shakiness index is determined to be less than a predetermined limit value.

26. The dental imaging system according to claim 21, wherein the central processing unit is further constructed to transmit a stop command to the intraoral camera, and
- wherein the stop command ends the specific time interval.

\* \* \* \* \*